United States Patent [19]

Karjala

[11] 4,041,150
[45] Aug. 9, 1977

[54] KERATIN MODIFYING AGENTS AND METHOD OF BENEFICIALLY MODIFYING FILAMENTOUS KERATIN MATERIALS

[75] Inventor: Sulo A. Karjala, Chicago, Ill.

[73] Assignee: Wilson Foods Corporation, Oklahoma City, Okla.

[21] Appl. No.: 147,623

[22] Filed: May 27, 1971

[51] Int. Cl.$^2$ ............................ A61K 7/09; A61K 7/11
[52] U.S. Cl. ................................ 424/71; 424/DIG. 2; 424/72
[58] Field of Search ....................... 424/71, 72, DIG. 2; 260/112 R; 8/128

[56] References Cited

U.S. PATENT DOCUMENTS

| | | | |
|---|---|---|---|
| 2,041,265 | 5/1939 | Orthner et al. | 260/112 R |
| 2,241,927 | 5/1941 | Sahyun | 260/112 R X |
| 2,479,382 | 8/1949 | Mace | 424/72 |
| 2,540,494 | 2/1951 | Schwarz | 424/72 X |
| 2,631,965 | 3/1953 | Schnell | 424/72 |
| 2,691,378 | 10/1954 | Oliva | 424/71 X |
| 2,738,304 | 3/1956 | Arnold | 424/72 |
| 3,683,939 | 8/1972 | Johnsen et al. | 132/7 |

*Primary Examiner*—Stanley J. Friedman
*Attorney, Agent, or Firm*—Dressler, Goldsmith, Clement, Gordon & Shore, Ltd.

[57] ABSTRACT

The invention relates to materials which are beneficiating agent derivatives for bonding a beneficiating agent to filamentous keratins such as hair and wool and effect modification of the filamentous keratins by being chemically coupled thereto so as to become an integral part thereof. The materials for improving the properties of filamentous keratins comprise polypeptides having intact disulfide linkages and having an agent molecularly joined thereto through a bond independent of the disulfide linkages to form a polypeptide derivative. Such a derivative is chemically bonded to the filamentous keratins by a two-step process wherein disulfide linkages of both the derivatives and the filamentous keratins are split by the action of a reducing agent and disulfide linkages are then reformed by action of an oxidizing agent whereby at least some of the sulfhydryl groups formed by the action on the derivatives of the reducing agent are bonded to sulfhydryl groups of the filamentous keratins.

9 Claims, No Drawings

KERATIN MODIFYING AGENTS AND METHOD OF BENEFICIALLY MODIFYING FILAMENTOUS KERATIN MATERIALS

This invention relates to materials for modification of filamentous keratins such as hair or wool. More particularly, it relates to materials comprising beneficiating agents for filamentous keratins coupled covalently to said keratins, the beneficiating agent being molecularly bound to the keratins by means of a coupling agent, which is the product of hydrolysis of keratin materials, to which a beneficiating agent is coupled through a bond independent of the disulfide linkages thereof to form a derivative. Still more particularly, it relates to a method of treating hair or wool wherein the derivatives for improving the properties of filamentous keratins are rendered an integral part of the keratins by treating the keratins with an aqueous solution of the derivative plus a reducing agent, followed by treating the resultant reaction products with an oxidizing agent.

In accordance with this invention, a water soluble product of partial hydrolysis of keratinaceous material containing intact disulfide linkages is molecularly coupled through bonds independent of the disulfide linkages to a beneficiating agent capable of imparting a desired property to the filamentous keratins, to form a water or alkali soluble derivative. The derivatives are then chemically bonded to render them an integral part of the filamentous keratins by a two-step process involving contacting the filamentous keratins with a solution of derivatives and a reducing agent adapted to effect splitting of disulfide linkages present in both the filamentous keratins and the derivatives to produce terminal sulfhydryl groups and then reforming disulfide linkages by treatment with an aqueous solution of oxidizing agents whereby at least some of the sulfhydryl groups of the derivatives are coupled with sulfhydryl groups of the filamentous keratins.

Filamentous keratins have been treated in numerous ways to improve the properties and characteristics thereof. Such treatments generally involve absorption or absorption of the agents or reaction with chemicals. The disadvantages of such treatments are that water soluble agents are not adsorbable or absorbable to the filamentous keratins in appreciable quantity and the adherenece is so weak that rinsing quickly removes significant amounts of the agents. The disadvantages of reactions with chemicals has been the damage to the fibers such as loss of weight and strength and rendering the fibers brittle.

A typical example of reaction with chemicals is permanent waving of human hair. It is well known that human hair can be set into a permanent wave establishing a stress on the hair in the form of the desired wave, applying reducing agent such as ammonium thioglycolate for a short time, rinsing out the reagent, and then treating the hair with a mild oxidizing agent such as sodium bromate or hydrogen peroxide. During treatment with the reducing agent, the stress in the hair is minimized by the opening up of the cystine disulfide linkages. Upon oxidation, the cystine linkages are again formed by closing of the disulfide linkages, but now the closure occurs not with the original sulfhydryl groups liberated, but with those which have been brought into greater proximity as a result of the stress. Thus, the hair strand is reformed but it now retains the new waved structure. This remains as a permanent feature of the hair strands until a new waving procedure is carried out, or until the hair strands grow out. However, repeated treatment of hair with reducing and oxidizing agents is damaging to the hair, particularly if the hair has been bleached. There is a marked loss in weight in the hair strands, and the hair becomes weak and brittle and difficult to comb.

Typical examples of reactions of animal hair with chemicals is illustrated by the dyeing process. In the treatment of wool, it is generally necessary to treat the wool with the dye in water at the boiling point to insure fastness of the dye with a result of weakening of the wool fibers. Once the wool is dyed with a fast dye, the color can no longer be removed readily and color removal can also have a weakening effect on the fibers.

Now it has been discovered, that agents capable of imparting a desired property to filamentous keratins can be made a stable and integral part of the keratin fibers by molecularly joining the agents to an organic disulfide coupling agent through a bond independent of the disulfide linkages and chemically bonding the coupling agent to the filamentous keratins by a two-step process involving splitting of disulfide linkages in both the coupling agent and filamentous keratins and then reforming disulfide linkages whereby at least some of the sulfhydryl groups of the coupling agent produced by the splitting action are bonded to sulfhydryl groups of the filamentous keratins.

In accordance with one embodiment of the invention, the method of treating filamentous keratins to make beneficiating agents an integral part thereof comprises incorporating a beneficiating agent derivative, which is a product of chemically coupling said agent to a water soluble product of partial hydrolysis of keratinaceous materials with acid to a peptide state retaining a substantial portion of intact disulfide linkages, through a bond independent of the disulfide linkages, into an aqueous solution of reducing agent of the type adapted to effect cleavage of disulfide linkages to form an aqueous composition for modification of filamentous keratins, contacting the filamentous keratins with said aqueous composition, and then after removal of excess reducing agent aqueous solution, contacting the aqueous composition treated filamentous keratins with a solution of oxidizing agent whereby at least some of sulfhydryl groups of the filamentous keratins produced by the cleavage action, induced by the treatment with the solution of reducing agent, are bonded to sulfhydryl groups of said derivative.

More in detail, in a preferred embodiment of the invention water or alkali soluble keratin polypeptide derivatives are produced as illustrated in examples hereinafter set forth and the derivatives are dissolved in a solution of a reducing agent such as ammonium thioglycolate, the cystine disulfide linkages being opened in the same way as those in the intact human hair or wool. Upon oxidation, a competition occurs between the sulfhydryl groups in the polypeptide an those in the intact hair, and a substantial portion of the linkages formed are now with keratin polypeptides. These polypeptides then become an integral part of the hair, since they have been bound to the hair or wool through a chemical covalent linkage. They then cannot be washed out or rinsed out with water, shampoo, acids, alkalis, or any organic solvents. They are attached as permanently as the linkages formed in the permanent wave.

Proof that the derivatives of keratin hydrolysis products can be chemically bonded to, for example, hair, is clearly demonstrated by treatment of hair with keratin polypeptides through their free amino groups to a diazotized dye. When human hair is treated with an aqueous solution of dye-coupled polypeptide containing a buffer salt to adjust the pH to about 9.2 and then washed with water, all of the dye-coupled polypeptide is removed and physical sorption is negligible. On the other hand, if the dye-coupled polypeptide is dissolved in an aqueous solution of ammonium thioglycolate of pH of about 9.2 and the human hair treated with the solution, excess solution is drained off and the treated human hair oxidized by treatment with aqueous solution of an oxidant such as sodium bromate, the hair strands have a color, none of which can be washed out with water, detergents, acids, alkalis or organic solvents.

Coupling of the dye-keratin polypeptide derivative with the hair or wool occurs at room temperature, and there is no necessity for heating the reaction mixture in boiling water. The extent of linkage of the dye-keratin polypeptide complex to the hair or wool is a function of the concentration of the complex in the reducing solution, and the reaction time used. Thus by modifying the conditions, any shade or tint of the dye can be obtained.

Wool can be modified in the form of yarn, or after weaving. Permanent prints can be made on wool if, for example, dry virgin wool flannel is treated with solutions of the keratin-dye complex in a reducing solution by means of a printing roller in which the design is transferred to the flannel, dried and subjected to a flow of air to obtain atmospheric oxidation, or passed through a dilute solution of mild oxidant, washed, and dried by normal means.

As has been pointed out above, the modification impressed on the hair or wool is permanent and is not removed by the ordinary rinse or shampoo treatments. There is one method, however, by which the modified keratin polypeptide can be substantially removed from the hair or wool products. This method is to treat the hair or wool product with thioglycolate alone, in order to reopen the disulfide linkages, wash the product well with water, and reoxidize with a mild oxidant. However, since repeated reductant and oxidant treatments tend to degrade the hair or wool, it is preferred to inhibit the degradation by adding unmodified keratin polypeptide to the reductant, so the modified derivative is replaced substantially by unmodified keratin polypeptides which have the ability to minimize the damage to hair or wool of such chemical actions.

Many types of derivatives of hydrolysis products can be made which can be coupled to hair or wool, the only restrictions being that the modifying compound does not destroy the disulfide linkage of the keratin polypeptide or cystine, that it forms a stable covalent bond with the polypeptide or cystine, and that it yields a coupled product soluble in the alkaline aqueous reducing agent solution used to open up the disulfide linkages.

As used herein, the terms have the following meanings:

Filamentous keratins means strands of hair, either human hair or animal hair, such as wool, alpaca, camel's hair, etc., which are strands of keratin fibers surmounted by a scaly cuticle of keratin protein. Typical keratinaceous starting materials for production of hydrolysis products which act as the coupling agent are human hair, hog hair, horn meal, feathers, cattle hair, etc. Acids useful for partial hydrolysis of keratinaceous materials are phosphoric acid, phosphorous acid, citric acid, tartaric acid, and the like. Reducing agents, useful for splitting the disulfide bonds, are thioglycolate salts such as ammonium and sodium thioglycolate, mercaptoethanol, sodium hydrosulfite, sodium formaldehyde sulfoxylate, sodium sulfite, etc. Useful oxidizing agents for reforming disulfide linkages from sulfhydryl groups are sodium bromate, hydrogen peroxide, atmospheric oxygen, etc. Beneficiating agents may be compounds which impart desired characteristics or properties to keratin fibers or keratin substrates such as woven wool or alpaca cloth or agents which form hydrolyzate derivatives capable of imparting unique properties. Such agents may be a dye, such as the dinitrophenyl derivative which imparts a golden color to hair, or a coloring-agent bearing derivative which is a product of reaction of a compound selected from the group consisting of a dye or a dye intermediate containing a free amino group capable of being diazotized to produce a diazo group for effecting coupling to said polypeptide, a dye mordant such as dextrin which enhances adsorption of dyes, etc., an agent such as the glyoxal or glutaraldehyde agents, the keratin polypeptide derivatives of which are anti-shrinking agents, and agents, the derivative of which will impart properties such as mothproofing and anti-wrinkling, etc. By a molecularly joined beneficiating agent, is meant the agent per se is joined through a reactive group or the agent is adapted by known means such as diazotization to form a diazonium salt which will be a reactable group and joined to the hydrolysis product coupling agent through reaction of the agent's reactable group, with a group such as a free amino group of the hydrolysis products.

The compositions with which filamentous keratins such as hair or wool are treated to effect bonding of a beneficiating agent-keratin hydrolysis peptide derivative to the hair strands comprises water, 4% to 8% by weight of reducing agent adapted to effect cleavage of disulfide linkages and from 0.1% to 25% by weight of said derivative of disulfide linkage-containing peptide product of partial hydrolysis of keratinaceous materials with acid under conditions to leave a substantial portion of the disulfide linkages intact.

The invention will be further understood from the foolowing examples which are given by way of illustration and without any intention that the invention be limited thereto.

EXAMPLE I

A hydrolysis product usable as a coupling agent for bonding beneficiating agents to filamentous keratins may be prepared as follows:

A sample of 500 grams of air dried hog hair (approximately 10% $H_2O$) was heated in a stainless steel container for 3 hours at 60 pounds pressure with 100 ml (176 grams) of 85% $H_3PO_4$ (orthophosphoric acid) in 3000 ml of water. This gave a final concentration of 5% $H_3PO_4$. The mixture from the autoclave, while still warm, was filtered, ad the dark brown pad of humin residue and undissolved hair was washed and dried. It weighed 90 grams so approximately 80% of the hair had been solubilized.

The cooled filtrate had a pH of 3.0 and precipitated 44 grams of protein. An additional 35 grams, for a total of 79 grams was obtained on adjustment of the pH to 4.0. Evaporation of the final filtrate in a vacuum after neutralization to pH 6.5 with calcium carbonate yielded a light colored concentrated solution of the water-soluble keratin polypeptides.

Derivatives if the peptide product of hydrolysis of Example I may be prepared and utilized for modification of filamentous keratins as shown by the following examples.

EXAMPLE II

A lauroyl derivative of a keratin polypeptide sample was prepared in known manner from lauroyl anhydride. The product was dissolved in 6% ammonium thioglycolate and coils of medium bleached hair strands were placed in the solution for 15 minutes, with similar coils of hair being placed in lauroyl keratin polypeptide solution in pH 9.2 borate-phosphate buffer. The thioglycolate-treated coils were then drained, oxidized for 5 minutes with 1.5% sodium bromate solution, and both sets of hair coils were then washed with water, detergent, acetone, alcohol, and finally ether.

The coils were then heated in a boiling water bath with 1 M sodium hydroxide to break down the proteins and polypeptides. The solutions resulting from hydroxide hydrolysis of the coils of treated hair after acidification to a pH of about 4 with hydrochloric acid, were extracted with petroleum ether, the extracts were dried and concentrated. The concentrated solutions from the lauroyl peptide-thioglycolate procedure gave a strong peak for lauric acid by gas chromatography while the control solution showed only a very small peak, which may have arisen from incomplete defatting of the hair prior to treatment.

Similar results were obtained when the myristoyl derivative of a keratin polypeptide was run in the same way.

This chromatograph test indicates that the lauric derivative was not leachable from the hair when coupled thereto by the thioglycolate treatment.

EXAMPLE III

Cystine was converted to dinitrophenylcystine by a known reaction with fluorodinitrobenzene. The product was crystallized from alcohol, dissolved in ammonium thioglycolate, in an amount to produce a 10% solution. Swatches of wool flannel and coils of hair were immersed in the solution for a short time, drained, and the keratin samples oxidized with dilute sodium bromate, washed with water, detergent, and organic solvents. The bright golden color in the sample was impervious to all solvents such as water, acetone, alcohol, ether, etc., which did not destroy the wool or hair swatches.

Similar results were obtained when keratin polypeptides, prepared as described in Example I, were converted to dinitrophenyl derivatives by the same reaction procedure.

EXAMPLE IV

A sample of dextrin was converted by known means to dextrin anthranilate by reaction with isatoic anhydride. The amino group of the anthranilyl radical was diazotized and the diazonium salt was coupled with a keratin hydrolyzate prepared by the partial hydrolysis of hog hair with phosphoric acid. The derivative product, an anthranilyl dextrin keratin polypeptide, was recovered by dialysis to remove salts, followed by lyophilization. Samples of wool, treated with 8% ammonium thioglycolate solution containing the dextrin derivative as a solute, for 15 to 30 minutes, followed by oxidation with 1.5% sodium bromate solution, washing with water and drying with acetone, showed no visual differences, but a portion thus treated gave a distinct carbohydrate test with anthrone reagent, while a control sample prepared by adsorption of the dextrin derivative from an aqueous 9.2 pH buffer solution showed a negative test. Thus, the carbohydrate definitely was coupled to the wool by the described procedure.

Samples of the treated wool and of control wool were treated at room temperature with the dye Wool Violet 4B. Upon washing with water, the dye was leached out of the control sample to a greater extent than from the dextrinized sample. Two treatments with water in a boiling water bath removed essentially all of the color from the control swatch, while the dextrinized sample was still deeply colored.

EXAMPLE V

Cystine was converted by known means to cystine palmitate by reaction with palmitoyl chloride. The product was soluble in hot alchohol, and could be crystallized from this solvent. It was soluble to 10% concentration in 8% ammonium thioglycolate at pH 9.2, and set to a gel upon cooling. Four swatches of virgin wool flannel were immersed in two portions of the reagent, one portion being warmed to 45° C. to effect solution before two wool swatches were added, after which the material was allowed to stand at room temperature for one hour. The second portion was maintained at 45° C. with the wool swatches for one hour. All the swatches were then removed, the excess reagent drained or pressed out, and the swatches were oxidized for 5 minutes with 1.5% sodium bromate. All swatches had a somewhat whiter color than the original material, but the heated swatches showed some shrinkage after five washings of each swatch in boiling alcohol to remove extraneous cystine palmitate.

One swatch each of the unheated and heated samples was now treated with 8% ammonium thioglycolate at pH 9.2 with added cystine to aid in displacing the cystine palmitate. The swatches were treated as in the initial procedure, washed five times with boiling alcohol, and dried.

Alkaline hydrolysis of the swatches, followed by acidification and extraction of the palmitic acid fraction, if present, did indeed demonstrate that cystine palmitate has been chemically bound to the wool, the heated swatch reacting to couple approximately three times more of the derivative than did the unheated swatch.

After treatment with thioglycolate, both swatches showed a decrease in cystine palmitate content by 25 to 30%. The washings of the second thioglycolate treatment were combined, the cystine palmitate was isolated and hydrolyzed, an a positive test for palmitic acid was obtained, indicating again that cystine palmitate had been removed from the wool by selective chemical reaction.

EXAMPLE VI

A sample of sorbitol was converted to the anthranilic acid derivative and the diazotized product was coupled with a keratin hydrolyzate as in Example III. The product was soluble in alkali but could be precipitated with acid to give a dark red product. Wool swatches treated with this material dissolved in ammonium thioglycolate, as described in previous examples, and reoxidized give yellow-brown materials as a result of the color of the coupled product. The color could not be removed by treatment with normal inorganic or organic solvents, but a portion could be removed by a second treatment with ammonium thioglycolate in the absence of the sorbitol derivative. A portion of the initially-treated wool swatch gave a positive color reaction for carbohydrates, showing that coupling to the wool had occurred.

EXAMPLE VII

A sample of 10 grams of keratin polypeptides was dissolved in 100 ml of water, the pH adjusted to 8.0 with concentrated ammonia, and the mixture was heated to 45° C., followed by the addition of 2 ml of 40% glyoxal (0.8 grams) diluted to 10 ml with water. The mixture was stirred for 2 hours at 45° to 50° C., with adjustment of the pH to 7.5 to 8.0 as required, concentrated in a vacuum to 25 to 30 ml and poured into 600 ml of acetone. The gummy precipitate was then rubbed with a stirring rod until it granulated, after which it was filtered, the solid ground to a powder in a mortar under acetone, filtered again, and dried.

This procedure is a known, standard method for the reaction of dialdehydes with proteins, and higher or lower degrees of condensation and polymerization can be obtained by variations in the concentration of the reagents used.

The results of chemically bonding the products of Examples I, III and VII to human hair and wool and the results of treatment of the products of the initial chemical bonding with a solution of the reducing agent with or without the product of Example I (keratin peptide mixture) are shown in Table I.

EXAMPLE VIII

A run similar to that described in Example VII was made except that the reagent used was 4 ml of 25% glutaraldehyde (1.0 grams) in place of the glyoxal. In this case also, variations in concentration of the reactants can give products of higher or lower degrees of polymerization.

EXAMPLE IX

Swatches of medium bleached hair were treated with solutions of 5% of the glyoxal and glutaraldehyde-condensation products described in Examples VII and VIII, each in 4% ammonium thioglycolate solution for 15 minutes. Similar swatches of virgin white hair were similarly treated for 30 minutes. After reoxidation with sodium bromate, washing, and drying, the medium bleached hair swatches were somewhat stiff, indicating some hair degradation under these conditions. The virgin hair swatches were soft and smooth. Treatment of bleached hair swatches with the same reagents described above, but with the addition of 5% of the keratin polypeptides of Examples I, to the solution gave hair swatches which were also smooth and soft, demonstrating the protective effect of the added keratin polypeptides upon the bleached, weakened hair.

Treatment of wool swatches with the above solutions without added keratin peptides gave products of yellow to brown color, since the condensation products were

TABLE I

| | Initial Treatment | | | Subsequent Treatment | | |
|---|---|---|---|---|---|---|
| Sample and Reaction Time | Keratin Poly-peptide | Thio-glycolate | Weight Change | Keratin Poly-peptide | Thio-glycolate | Weight Change |
| Medium Bleached Hair ½ Hour | 25% | 4% | +2.4% | | | |
| | 25% | 4% | +3.6% | 0 | 4% | −9.3% |
| | 0 | 4% | −11.0% | | | |
| Wool Flannel ½ Hour | DNP - Keratin Polypeptide | | | | | |
| | 1% | 0 | +1.1% | | | |
| | 1% | 8% | +3.2% | | | |
| | 1% | 8% | +3.0% | 0 | 8% | −2.6% |
| Medium Bleached Hair 10 Minutes | 0 | 8% | −6.8% | | | |
| | 0.1% | 8% | +1.9% | 0 | 8% | −7.4% |
| | 0.1% | 8% | +1.6% | | | |
| Wool Flannel 1 Hour | Glyoxal-Polypeptide | | | | | |
| | 8% | 8% | +3.65% | | | |
| | 8% | 8% | +4.4 % | 0 | 8% | −0.6% |

These results are based on weight changes, so relative differences in one series are comparable. However, it is not always possible to compare the results in one series with those in another, since the weight changes are occasionally modified by changes in moisture content due to changes in relative humidity.

After treatment with keratin polypeptide, the samples were washed thoroughly with water and detergent, dried with acetone, and finally air-dried.

After treatment with ammonium thioglycolate, the samples were washed with water, oxidized for 5 minutes with 1.5% sodium bromate solution, washed again with water and detergent, dried with acetone, followed by air-drying.

After treatment with mixtures of keratin polypeptides or their modified products plus ammonium thioglycolate, the samples were drained a short time to remove the excess solution, after which they were oxidized with 1.5% sodium bromate solution for 5 minutes, and washed and dried as above.

darker in color than the original peptides. In the presence of 5% added keratin polypeptides, the final color was intermediate between the swatches treated without added keratin peptides and the control swatches.

EXAMPLE X

A so-called oxidation-type dye was prepared by mixing 10 grams of paraphenylenediamine and 1 gram of pyrogallol in 50 ml of water, heating at 75° C. for 30 minutes and cooling to 40° C. The mixture was adjusted to pH 9.2 with ammonia, treated with 35% hydrogen peroxide solution to give a final peroxide concentration of 3%, and warmed at 40° for 30 minutes, to this mixture was added 10 grams of keratin polypeptides. An exothermic reaction occurred, raising the temperature to 75°. After cooling, the liquid reaction product was filtered from unreacted paraphenylenediamine, concentrated to small volume and poured into acetone. The granular material was filtered, washed with acetone and dried.

The peptide dye complex was dissolved in a 6% ammonium thioglycolate in an amount to produce a 5% solution. Swatches of wool flannel and coils of hair, i.e., keratin bases, were immersed in the glycolate solution, drained of solution and oxidized with a 5% sodium bromate solution. Treated wool flannel and hair was then washed with water, detergent, alcohol and ether. The peptide-dye complex imparted a light brown color to the wool and hair and the color was not altered by treatment with washing agents, showing that the complex had been bonded to the keratin bases.

EXAMPLE XI

A sample of the pH 4.2 isoelectric precipitate of hog hair obtained from a digest of the hair with 6% oxalic acid at 50 pounds pressure for 3 hours is coupled by a known chemical reaction to diazotized 2.4 - dichlorosulfanilic acid. The product, a red-brown solid after acidification of the solution, filtration, and washing and drying with acetone, is insoluble in water but soluble in phosphate-borate buffer at pH 9.2. Human hair strands or wool swatches immersed in the solution and washed with water, detergent, and organic solvents are unchanged. None of the dye attaches to the keratin. If, however, the keratin polypeptide modified by coupling to the 2.4-dichlorosulfanilic acid is dissolved in ammonium thioglycolate, and hair is treated with an aqueous thioglycolate-derivative composition, the human hair strands or wool swatches become colored, and, after a short period of oxidation with sodium bromate or other oxidant are permanently dyed. Neither acids nor bases nor organic solvents remove the dye from the keratin.

A great advantage of this invention is that when highly toxic reagents would be necessary to develop a specific modification of human hair or wool and would thus be incapable of being used because of their toxicity or damaging effect on the hair or wool, these toxic and damaging reagents could be used for preparation of a modified keratin polypeptide, and the polypeptide derivative formed by the reaction could then readily be coupled to the hair or wool after the derivative had been isolated andpurified from the toxic reagents used in its preparation.

Although the best mode contemplated for carrying out the present invention has been herein shown and described, it will be apparent that modification and variation may be made without departing from what is regarded to be the subject matter of the invention as set forth in the appended claims.

I claim:

1. A method of modifying filamentous keratins which comprises contacting said keratins with an effective amount of an aqueous treating composition containing an effective amount of a reducing agent and 0.1 to 8% of a water or alkali-soluble reaction product of (1) a water-soluble product of acid hydrolysis of keratinaceous materials to a peptide state with (2) a beneficiating agent for said filamentous keratins capable of reacting with said water-soluble hydrolysis product through the formation of amide linkages, removing the excess aqueous treating composition from said keratins, and contacting the modified filamentous keratins with an effective amount of an aqueous solution of an oxidizing agent.

2. A method of modifying filamentous keratins which comprises contacting said keratins with an effective amount of an aqueous treating composition containing an effective amount of a reducing agent and 0.1 to 8% of a water or alkali-soluble reaction product of (1) a water-soluble product of acid hydrolysis of keratinaceous materials to a peptide state with (2) dextrin anthranilate, removing the excess aqueous treating composition from said keratins, and contacting the modified filamentous keratins with an effective amount of an aqueous solution of an oxidizing agent.

3. A method of modifying filamentous keratins which comprises contacting said keratins with an effective amount of a reducing agent and 0.1 to 8% of a water or alkali-soluble reaction product of (1) a water-soluble product of acid hydrolysis of keratinaceous materials to a peptide state with (2) a dialdehyde of the group consisting of glyoxal and glutaraldehyde, removing the excess aqueous treating composition from said keratins, and contacting the modified filamentous keratins with an effective amount of an aqueous solution of an oxidizing agent.

4. A method of modifying filamentous keratins which comprises contacting said keratins with an effective amount of an aqueous treating composition containing an effective amount of a reducing agent and 0.1 to 8% of a water or alkali-soluble reaction product of (1) a water-soluble product of acid hydrolysis of keratinaceous materials to a peptide state with a member of the group consisting of lauroyl anhydride and myristoyl anhydride, removing the excess aqueous treating composition from said keratins, and contacting the modified filamentous keratins with an effective amount of an aqueous solution of an oxidizing agent.

5. A method of treating filamentous keratins to make beneficiating agents an integral part thereof comprising reacting (1) a water-soluble product of acid hydrolysis of keratinaceous materials to a peptide state, said product containing reactive groups including free amino groups and retaining a substantial portion intact disulfide linkages, with (2) a beneficiating agent to form a water or alkali soluble derivative in which the beneficiating agent is covalently coupled to the hydrolysis product, adding to said soluble derivative (3) an aqueous solution of a reducing agent of the type adapted to effect cleavage of disulfide linkages to thereby produce an aqueous treating composition containing excess reducing agent, contacting the filamentous keratins with said aqueous treating composition to produce a mixture having split disulfide linkages in both the hydrolysis product derivative and the filamentous keratins, and then, after removal of excess reducing agent aqueous composition, contacting the treated filamentous keratins with a solution of oxidizing agent whereby at least some of the sulfhydryl groups of the hydrolysis product derivative are coupled with sulfhydryl groups of said filamentous keratins.

6. A composition for modifying filamentous keratins which comprises a mixture of an aqueous treating composition containing an effective amount of a reducing agent with 0.1 to 8% of a water or alkali-soluble reaction product of (1) a water-soluble product of acid hydrolysis of keratinaceous materials to a piptide state with (2) a beneficiating agent for said filamentous keratins capable of reacting with said water-soluble hydrolysis product through the formation of amide linkages.

7. A composition for modifying filamentous keratins which comprises a mixture of an aqueous treating composition containing an effective amount of a reducing agent with 0.1 to 8% of a water or alkali-soluble reaction product of (1) a water-soluble product of acid hydrolysis of keratinaceous materials to a peptide state with (2) dextrin anthranilate.

8. A composition for modifying filamentous keratins which comprises a mixture of an aqueous treating composition containing an effective amount of a reducing agent with 0.1 to lb 8% of a water or alkali-soluble reaction product of (1) a water-soluble product of acid hydrolysis of keratinaceous materials to a piptide state with (2) a dialdehyde of the group consisting of glyoxal and glutaraldehyde.

9. A composition for modifying filamentous keratins which comprises a mixture of an aqueous treating composition containing an effective amount of a reducing agent with 0.1 to 8% of a water or alkali-soluble reaction product of (1) a water-soluble product of acid hydrolysis of keratinaceous materials to a piptide state with a member of the group consisting of lauroyl anhydride and myristoyl anhydride.

* * * * *

UNITED STATES PATENT AND TRADEMARK OFFICE
CERTIFICATE OF CORRECTION

PATENT NO. : 4,041,150  (page 1 of 2)
DATED : August 9, 1977
INVENTOR(S) : Sula A. Karjala It is certified that error appears in the above-identified patent and that said Letters Patent are hereby corrected as shown below:

Col. 1, line 54, insert -- by -- after "wave".

Col. 2, line 58, "an should be -- and --.

Col. 3, line 2, insert -- coupled -- after "polypeptides".

Col. 4, line 44, "foolowing" should be -- following --.

line 58, "ad" should be -- and --.

Col. 5, line 1, "if" should be -- of --.

Col. 7, line 12, "45°" should be -- 45°C --.

Col. 9, line 43, "andpurified" should be -- and purified --.

Col. 10, line 11, insert -- an aqueous treating composition containing an effective amount of -- after "amount of".

UNITED STATES PATENT AND TRADEMARK OFFICE
CERTIFICATE OF CORRECTION

PATENT NO. : 4,041,150
DATED : August 9, 1977
INVENTOR(S) : Sula A. Karjala

It is certified that error appears in the above-identified patent and that said Letters Patent are hereby corrected as shown below:

(Page 2 of 2)

Col. 11, line 6, delete "1b".

line 8, change "piptide" to -- peptide --.

Col. 12, line 9, change "piptide" to -- peptide --.

Signed and Sealed this

Twenty-seventh Day of December 1977

[SEAL]

Attest:

RUTH C. MASON
Attesting Officer

LUTRELLE F. PARKER
Acting Commissioner of Patents and Trademarks